US010154805B2

United States Patent
Biederman et al.

(10) Patent No.: US 10,154,805 B2
(45) Date of Patent: Dec. 18, 2018

(54) DISPOSABLE GLUCOSE BIOSENSOR INCLUDING AN ACTIVITY SENSOR

(71) Applicant: Verily Life Sciences LLC, South San Francisco, CA (US)

(72) Inventors: William Biederman, San Francisco, CA (US); Miguel Drumond, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 15/725,562

(22) Filed: Oct. 5, 2017

(65) Prior Publication Data

US 2018/0103882 A1 Apr. 19, 2018

Related U.S. Application Data

(60) Provisional application No. 62/407,670, filed on Oct. 13, 2016.

(51) Int. Cl.
| | |
|---|---|
| *G01N 27/327* | (2006.01) |
| *A61B 5/145* | (2006.01) |
| *C12Q 1/00* | (2006.01) |
| *G06F 19/00* | (2018.01) |

(Continued)

(52) U.S. Cl.
CPC .......... *A61B 5/14532* (2013.01); *C12Q 1/001* (2013.01); *C12Q 1/006* (2013.01); *G01N 27/3275* (2013.01); *G06F 19/00* (2013.01); *A61B 5/0002* (2013.01);

(Continued)

(58) Field of Classification Search
CPC ................ G01N 27/3275; C12Q 1/001; G06F 19/3418; H04L 7/0079; A61M 2205/3592; A61B 5/14532; A61B 5/0002
See application file for complete search history.

(56) References Cited

U.S. PATENT DOCUMENTS

| | | | |
|---|---|---|---|
| 6,175,752 B1 * | 1/2001 | Say | A61B 5/14532 128/903 |
| 6,579,690 B1 * | 6/2003 | Bonnecaze | A61B 5/0031 435/14 |
| 8,771,183 B2 | 7/2014 | Sloan et al. | |

(Continued)

FOREIGN PATENT DOCUMENTS

WO    2015073878    5/2015

OTHER PUBLICATIONS

International Application No. PCT/US2017/055784, "International Search Report and Written Opinion", Feb. 28, 2018, 7 pages.

*Primary Examiner* — J. Christopher Ball
(74) *Attorney, Agent, or Firm* — Kilpatrick Townsend & Stockton LLP (57) ABSTRACT

Example disposable biosensor devices having an activity sensor are disclosed. One example device includes a disposable biosensor that has a first electrode having a distal end to be inserted into a subcutaneous layer beneath a person's skin, the first electrode having a reactive material disposed on the distal end, and a second electrode. The disposable biosensor device also includes an activity sensor that can be activated upon an activity by the person, the activity sensor for detecting the activity and providing data about the activity. The disposable biosensor also includes a radio frequency transmitter for transmitting data obtained from the first or second electrode and the activity sensor.

17 Claims, 3 Drawing Sheets

(51) Int. Cl.
 *H04L 7/00* (2006.01)
 *A61B 5/00* (2006.01)
(52) U.S. Cl.
 CPC . *A61M 2205/3592* (2013.01); *G06F 19/3418* (2013.01); *H04L 7/0079* (2013.01)

(56) References Cited

U.S. PATENT DOCUMENTS

| | | |
|---|---|---|
| 9,858,328 B2 | 1/2018 | Gibson et al. |
| 2005/0280531 A1 | 12/2005 | Fadem et al. |
| 2009/0240120 A1* | 9/2009 | Mensinger ............ A61B 5/7445 600/301 |
| 2009/0255810 A1 | 10/2009 | Ichino et al. |
| 2010/0049004 A1* | 2/2010 | Edman ................. A61B 5/1118 600/300 |
| 2010/0198142 A1* | 8/2010 | Sloan ................ A61B 5/14532 604/66 |
| 2010/0213080 A1 | 8/2010 | Celentano et al. |
| 2011/0152637 A1 | 6/2011 | Kateraas et al. |
| 2012/0059664 A1 | 3/2012 | Georgiev et al. |
| 2013/0310658 A1 | 11/2013 | Ricks et al. |

* cited by examiner

DISPOSABLE GLUCOSE BIOSENSOR INCLUDING AN ACTIVITY SENSOR

CROSS-REFERENCE TO RELATED APPLICATIONS

The present application is related to and claims the benefit of priority of U.S. Provisional Application No. 62/407,670, filed Oct. 13, 2016, entitled "DISPOSABLE GLUCOSE BIOSENSOR INCLUDING AN ACTIVITY SENSOR", the entirety of which is incorporated herein by reference.

FIELD

The present disclosure generally relates to invasive biometric sensors and more specifically to a disposable glucose biosensor that includes an activity sensor.

BACKGROUND

Physical activity (e.g., walking, running, jumping, etc.) can have various effects on a person's body including, for example, increasing or reducing the person's blood glucose level. For example, during physical activity, insulin in the person's blood stream may cause glucose to be absorbed by the person's body, which can reduce the person's blood glucose level. In some instances, the person's body may not produce enough insulin to cause the glucose to be absorbed or the person's body may otherwise not properly absorb the glucose, thus some people monitor their blood glucose levels and periodically administer insulin to help regulate them.

SUMMARY

Various examples are described for a disposable glucose biosensor that includes an activity sensor.

In one example, a device according to the present disclosure includes a disposable biosensor. The disposable biosensor includes: a first electrode having a distal end insertable into a subcutaneous layer beneath a patient's skin, the first electrode having a reactive material disposed on the distal end; a second electrode comprising a counter electrode to the first electrode; an activity sensor to sense activity and provide sensor information, the sensor information comprising information about a physical movement of the patient; and a radio frequency ("RF") transmitter in communication with the first and second electrodes and the activity sensor to transmit biosensor information.

In one example, a method according to the present disclosure includes: inserting a distal end of a first electrode of a disposable glucose biometric sensor into a subcutaneous layer beneath a patient's skin, the disposable glucose biometric sensor comprising an activity sensor and the first electrode having a reactive material disposed on the distal end; applying a second electrode of the disposable glucose biometric sensor to the patient, the second electrode comprising a counter electrode to the first electrode; receiving a glucose sensor signal from the first or second electrodes, the sensor signal indicating the patient's glucose level; receiving an activity sensor signal from the activity sensor, the activity sensor signal comprising information about a physical movement of the patient; and storing the patient's glucose level and information determined from the activity sensor signal.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of a disposable glucose biosensor that includes an activity sensor. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Figure 1:
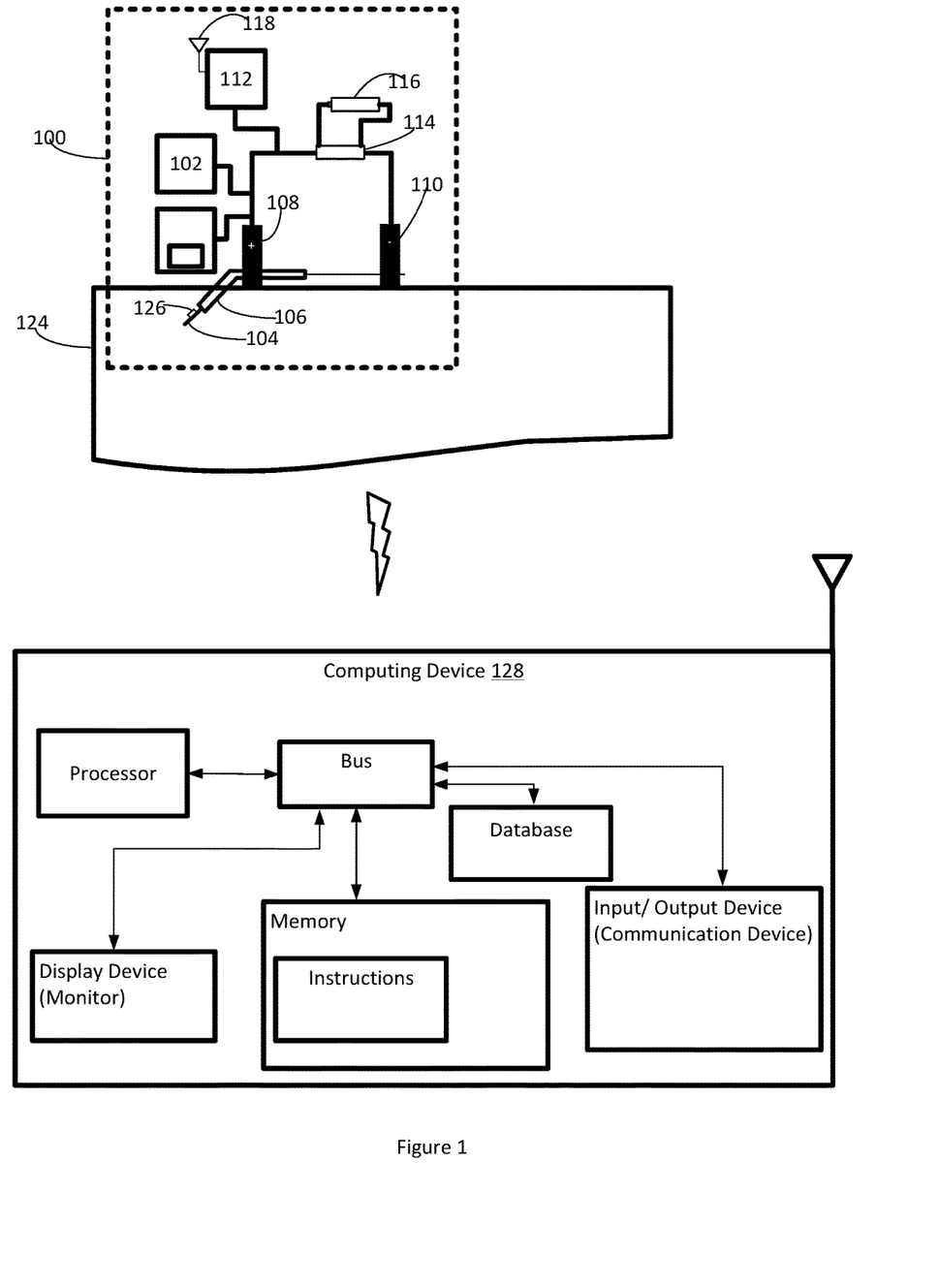
FIG. 1 shows an illustrative example of a disposable glucose biosensor that includes an activity sensor.

Illustrative Example of a Disposable Glucose Biosensor Including an Activity Sensor FIG. 1 shows an illustrative example of a disposable glucose biosensor 100 that includes an activity sensor 102. In this example, the disposable glucose biosensor 100 is an invasive glucose biosensor (e.g., a sensor that is inserted into a patient's skin 124 or other tissue) that senses glucose levels in the interstitial fluid beneath the patient's skin 124. The disposable glucose biosensor 100 also obtains information from the activity sensor 102 about an activity of the patient, which can be correlated with the sensed glucose levels and wirelessly communicated to another device for analysis. The disposable glucose biosensor 100 senses glucose levels and activity information for the duration of its usable life, which is dictated by the battery 116. Once the battery 116 is sufficiently depleted, any remaining data is read from the disposable glucose biosensor 100, and the disposable glucose biosensor 100 is removed from the patient and discarded. The patient then applies a new biosensor.

For example, the working electrode 104 and the counter electrode 106 are positioned under a patient's skin 124. In the example depicted in FIG. 1, the working electrode 104 is a platinum or platinum coated wire and the counter electrode 106 is a silver/silver-chloride ("Ag/AgCl") material that is coated or otherwise disposed on part of the working electrode 104 and inserted into the patient's skin 124 with the working electrode 104. One end of the working electrode 104 is inserted into the patient's skin 124 to expose the working electrode 104 to interstitial fluid beneath the patient's skin or surrounding other tissue, from which glucose readings or other readings may be sensed. The end of the working electrode 104 that is inserted into the patient's skin 124 includes a reactive material 126, which cause a reaction when that end of the working electrode 104 is inserted into the patient's skin 124. In this example, the reactive material 126 is a glucose oxidase ("GOX") coating that will react to glucose present within the patient's interstitial fluid to form a reaction product such as, for example, hydrogen peroxide. The battery 116 provides a voltage to the working electrode 104 or the counter electrode 106 via the conductive contacts 108, 110, which generates an electrical current based on the amount of the reaction product generated by the glucose and GOX reaction.

In this illustrative example, the activity sensor 102 is turned on in response to the patient's activity. For example, the activity sensor 102 powers on or becomes enabled when the patient begins to walk, jog, run, etc. The activity sensor 102 also detects data associated with the activity and the data is wirelessly communicated to a remote device for analysis (e.g., the computing device 128) via the transmitter 112 and antenna 118. As an example, the activity sensor 102 is an accelerometer that detects the patient's motion while the patient is jogging and a time or duration of the jog. The activity sensor 102 stores the data about the patient's activity and, when possible, transmits the data to the computing device 128, which determines a number of steps taken by the patient, an intensity of the activity, etc. based on the data from the activity sensor 102.

The remote device receives the data about the patient's activity and data about the sensed glucose levels and stores the data to allow the remote device to analyze data about a particular activity that the patient is engaged in and the patient's blood glucose levels. For example, the remote device can determine an effect of the patient's activity on the amount of glucose present in the patient's interstitial fluid and determine whether to output an alarm based on the determination. Once the data is transmitted to the remote device, or when the battery 116 of the disposable glucose biosensor 100 is depleted, the disposable glucose biosensor 100 is removed from the patient and discarded to allow the patient to apply another biosensor.

This illustrative example is given to introduce the reader to the general subject matter discussed herein and the disclosure is not limited to this example. The following sections describe various additional non-limiting examples and examples of systems and methods for disposable glucose biosensors that include an activity sensor.

Figure 2:
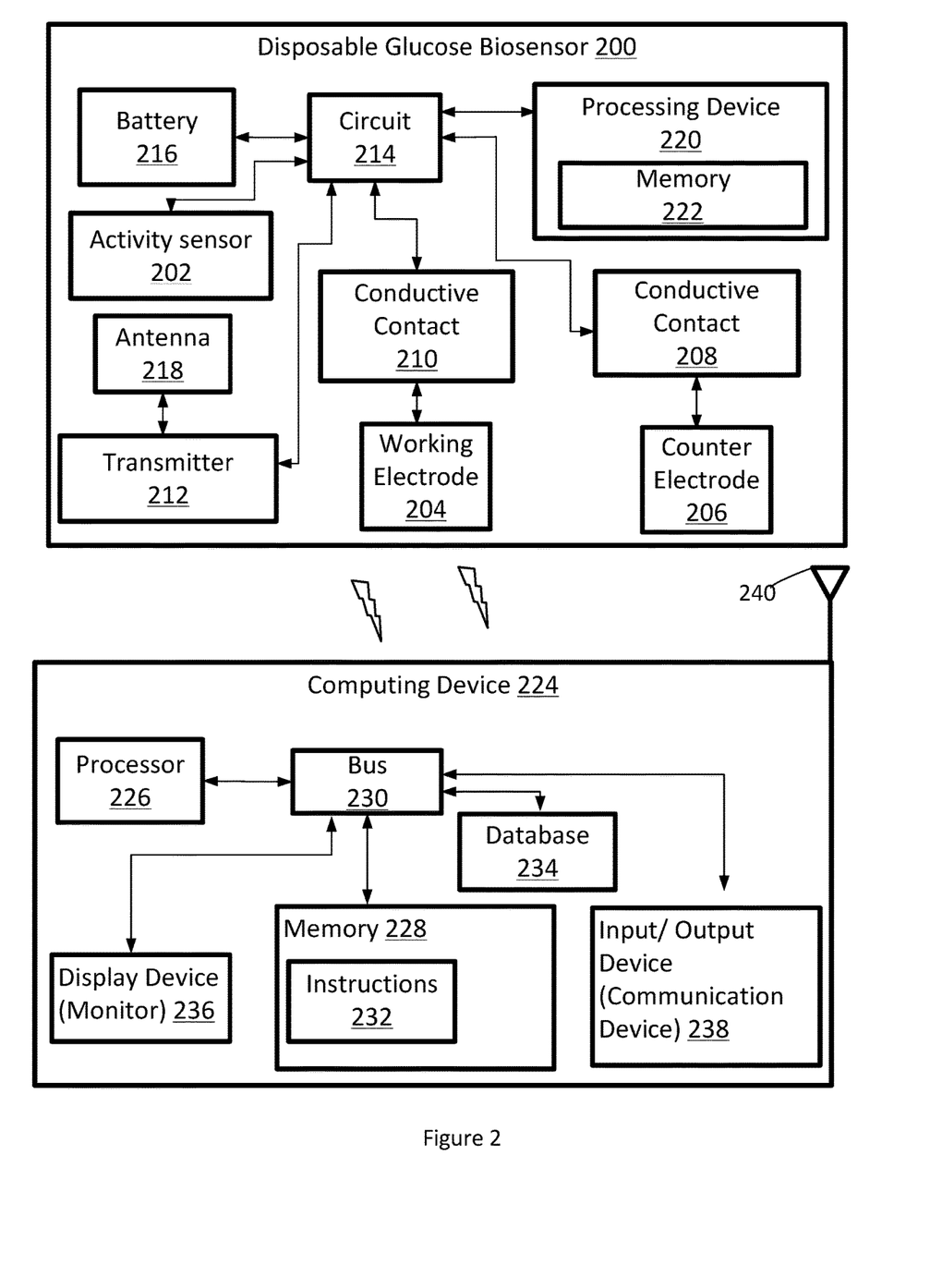
FIG. 2 is an example of a disposable biosensor that includes an activity sensor.

FIG. 2 is an example of a disposable biosensor 200 that includes an activity sensor 202. The disposable biosensor 200 shown in FIG. 2 also includes a working electrode 204, a counter electrode 206, conductive contacts 208, 210, a transmitter 212, a circuit 214, a battery 216, an antenna 218, and a processing device 220 that includes a memory 222.

Each of the activity sensor 202, the working electrode 204, the counter electrode 206, the conductive contacts 208, 210, and the transmitter 212 is electrically coupled to the battery 216 via the circuit 214 to receive a voltage from the battery 216. In some examples, the working electrode 204 and the counter electrode 206 can be used to determine a blood glucose level of a user of the disposable biosensor 200 and the activity sensor 202 can be used to monitor the user's activity. The transmitter 212 and the antenna 218 can be used to transmit data about the user's blood glucose levels and data about the user's activity to a remote device (e.g., a computing device 224) for analysis.

The disposable biosensor 200 is an invasive glucose biosensor (e.g., a sensor that is inserted into a patient's skin or other tissue) that senses glucose levels in the interstitial fluid beneath the patient's skin. The disposable biosensor 200 is also disposable and can be discarded after being used for a period of time (e.g., after the battery is drained below a threshold level). In some examples, the disposable biosensor 200 is a single-use biosensor that can be discarded after data about the patient's blood glucose levels or the patient's activity is transmitted to the remote device for analysis.

The activity sensor 202 is a device that can detect or provide data about an activity of a user of the disposable biosensor 200 (e.g., a patient). Examples of the activity sensor 202 include, but are not limited to, an accelerometer, a gyroscope, a temperature sensor, a heart rate sensor, an inertial measurement unit, and a galvanic skin response sensor. In some examples, an inertial measurement unit can include one or more accelerometers, gyroscopes, or magnetometers for detecting or measuring data about the user's specific force, linear motion, angular motion, angular velocity, linear acceleration, data about a magnetic field around the user, or any other data about an activity of the user of the disposable sensor 200. In some examples, the activity sensor 202 can be enabled (e.g., turned on) in response to activity by the user. As an example, the activity sensor 202 is an accelerometer that detects the user's motion when the user is engaged in an activity (e.g., detects the user's motion when the user starts walking, jogging, running, etc.) and becomes enabled in response to the detected motion. As another example, the activity sensor 102 is a galvanic skin response sensor that can detect an amount of sweat produced by the user during the activity such as, for example, when the user is running.

Data about the user's activity detected by the activity sensor 202 can be used to determine one or more parameters associated with the activity such as, for example, a type of the activity (e.g., whether the user is walking or running) an intensity of the activity (e.g., an acceleration of the user while the user is engaged in the activity, or a number of steps per second or per minute), a number of steps taken by the user during the activity, a duration of the activity, a temperature of the user during the activity, a heart rate of the user, a respiration rate of the user during the activity, a resting respiration rate of the user after the activity, an amount of sweat produced by the user during the activity, etc. For example, the activity sensor 202 provides data about the user's activity to the processing device 220 or the computing device 224, which can determine one or more parameters associated with the activity based on the data.

As an example, the activity sensor 202 can be an accelerometer that detects the user's motion when the user is running and data about the user's motion is transmitted to the processing device 220, which can determine a number of steps taken by the user while the user is running. For example, the processing device 220 can execute processor executable instructions stored in the memory 222 to determine the number of steps taken by the user based on the data from the activity sensor 202.

As another example, the activity sensor 202 can be a heart rate sensor that detects a heart rate of the user during an activity and data about the user's heart rate can be transmitted to the computing device 224, which can execute processor executable instructions 232 stored in a memory 228 of the computing device 224 to determine the type or intensity of the activity based on the data. For example, the computing device 224 can determine that the user is running or that the user is engaged in a high intensity activity based on the user having a high heart rate.

Although a single activity sensor 202 is shown in FIG. 2, some examples may use multiple activity sensors 202 of the same or different type and each may detect or provide data about an activity of a user of the disposable biosensor 200. While the example depicted in FIG. 2 shows a disposable biosensor 200 that includes two electrodes, any number of electrodes may be included in the disposable biosensor 200. For example, the disposable biosensor 200 may include three or more electrodes for sensing glucose levels in interstitial fluid beneath a person's skin or any suitable number of electrodes for sensing the glucose levels.

The working electrode 204 can be a platinum or platinum coated wire (e.g., a wire coated or electroplated with a layer of platinum), which can be of any size or shape. The working electrode 204 or a portion of the working electrode 204 can be inserted into a subcutaneous layer beneath a person's skin. The wire of the working electrode 204 can be of any material including, for example, a metal or plastic substrate. The working electrode 204 can be formed by applying a platinum coating to a base wire by any suitable technique, including, for example, electroplating or physical vapor deposition, including evaporation and sputtering techniques. While using platinum for a wire or coating for a wire may be suitable for a certain disposable glucose sensor, other materials may be used according to other examples. In some examples, the working electrode 204 includes a distal portion that can be inserted under a person's skin to allow the disposable biosensor 200 to detect the person's blood glucose levels.

The counter electrode 206 can be an Ag/AgCl material. In some examples, the counter electrode 206 is an Ag/AgCl material that is coated or otherwise disposed on part of the working electrode 204 and a portion of the counter electrode 206 can be inserted into the subcutaneous layer beneath a person's skin with part of the working electrode 204.

In some examples, the counter electrode 206 can be an Ag/AgCl patch coated with a layer of silver and the layer of silver can be converted to silver-chloride. In such examples, the counter electrode 206 can be physically separate from the working electrode and can be attached to a surface of the person's skin. In some examples, the counter electrode 206 can be attached to the surface of the person's skin at a distance or location away from the working electrode 204. Various methods and techniques can be used to coat the Ag/AgCl patch with the layer of silver and to convert the layer of silver to silver-chloride to form the counter electrode 206.

In another example, the counter electrode 206 can include a wire for insertion into the subcutaneous layer beneath the person's skin. For example, the counter electrode 206 can include an Ag/AgCl wire that can be inserted into the subcutaneous layer at a distance or location away from the working electrode 204.

The conductive contacts 208, 210 are each connected to one of the working electrode 204 or the counter electrode 206 to couple the working electrode 204 and the counter electrode 206 to one or more other devices (e.g., a transmitter 112, receiver, transceiver, a circuit 114, battery 116, etc.). In the example depicted in FIG. 2, the conductive contact 210 is connected to the working electrode 204 and the circuit 214 and the conductive contact 208 is connected to the counter electrode 206 and the circuit 214 to couple the working electrode 204 and the counter electrode 206 to the battery 216, the transmitter 212, the activity sensor 202 and the processing device 220. Each conductive contact 208, 210 can be a conductive rubber contact, but in other examples, other suitable conductive materials, such as, for example, metal, may be used.

The circuit 214, which can be an integrated circuit, a potentiostat, or any suitable electrical circuit, can be electrically coupled to the battery 216. In some examples, the battery 216 is electrically couplable to the conductive contacts 208, 210 via the circuit 214 or a switch. For example, the battery 216 may be initially electrically decoupled from the conductive contacts 208, 210 or from the circuit 214, but may be coupled by closing a switch. In some examples, the battery 216 may be electrically couplable to the conductive contacts 208, 210 via the circuit 214 or any electrical component, such as a potentiostat. In some examples, the circuit 214 or a component of the circuit 214 may be electrically decoupled from the conductive contacts 208, 210 as discussed above with respect to the battery 216 and may be coupled to the conductive contacts 208, 210 or the battery 216, e.g., by closing a switch. In some examples, the battery 216 can provide a voltage (e.g., a steady or constant voltage) to the circuit 214 and the circuit 214 can provide the voltage to the conductive contacts 208, 210.

The processing device 220 includes the memory 222 that includes instructions, which can be executed by the processing device 220 to perform one or more operations for determining an amount of glucose in a person's interstitial fluid based on sensor data from the transmitter 112. In some examples, the memory 222 also includes instructions that can be executed by the processing device 220 to perform one or more operations for determining one or more parameters associated with the person's activity based on data from the activity sensor 202.

In some examples, the processing device 220 may receive sensor data from the working electrode 204 and the counter electrode 206 and store the sensor data in the memory 222. For example, the processing device 220 may receive glucose sensor data and store the glucose sensor data and a time stamp or time indicator that corresponds to a time that the glucose sensor data is received by the processing device 220 in the memory 222. As an example, the processing device 220 may receive the glucose sensor data, generate a time stamp associated with the time the glucose sensor data is received, and store the glucose sensor data and the time stamp in the memory 222. As another example, the processing device 220 may receive activity data from the activity sensor 202, generate a time stamp associated with the activity data, and store the activity data and the time stamp associated with the activity data in the memory 222. As still another example, the processing device 220 may receive sensor data that includes both activity data and glucose sensor data, generate a time stamp associated with the sensor data, and store the sensor data, along with the time stamp associated with the sensor data in the memory 222. In some examples, the disposable biosensor 200 may transmit sensor data (e.g., glucose sensor data or activity data), along with a time stamp associated with the data to a remote device (e.g., the computing device 224) for analysis.

The transmitter 212 can be radio frequency ("RF") transmitter that is connected to the circuit 214 to receive the voltage from the battery 216. In some examples, the transmitter 212 can provide sensor data to a remote device (e.g., the computing device 224) by transmitting the data using the antenna 218. In some examples, the transmitter 212 and the antenna 218 can communicate using suitable communication techniques, such as, for example, radio frequency identification ("RFID"), near-field communication ("NFC"), or BlueTooth™. For example, a remote device with an RFID or NFC reader may be brought into proximity of the antenna 218 and cause the transmitter 212 to transmit sensor data to the remote device. The sensor data can include an amount of glucose in a person's interstitial fluid or sensor data from the transmitter 112 with which the remote device can determine the amount of glucose in a person's interstitial fluid. The sensor data may also include data about the person's activity detected by the activity sensor 202 with which the remote device can determine one or more parameters associated with the person's activity.

In some examples, the working electrode 204 and the counter electrode 206 can be positioned under a person's skin to determine the person's blood glucose levels. In another example, the working electrode 204 can be positioned under the person's skin and the counter electrode 206 can be a patch attached to a surface of the person's skin to for determining the person's blood glucose levels.

For example, a distal portion of the working electrode 204 can be inserted into the person's skin to expose the distal portion of the working electrode 204 to the person's interstitial fluid, from which glucose readings or other readings may be taken. The distal portion of the working electrode 204 can be any portion or length of the working electrode 204 that is opposite to the portion of the working electrode 204 that is attached to the disposable biosensor 200. The distal portion of the working electrode 204 that is inserted into the person's skin can include a reactive material disposed on the distal portion, which may react when the distal portion is inserted into the person's skin. For example, the reactive material can be a glucose oxidase ("GOX") coating disposed on the distal portion that will react to glucose present within the person's interstitial fluid. For example, when the working electrode 204 is inserted into the person's skin, the GOX may react with glucose in the person's interstitial fluid, which can create a reaction product such as, for example, hydrogen peroxide. A voltage can be applied to the working electrode 204 or the counter electrode 206 (e.g., from the battery 216 and via the circuit 214 and the conductive contacts 208, 210), which can generate an electrical current based on the amount of the reaction product generated by the glucose and GOX reaction. In this example, the reactive material is GOX, but in other examples, other suitable reactive materials may be applied on the distal portion of the working electrode 204.

As an illustrative example, the working electrode 204 can be connected to the conductive contact 210 and the counter electrode 206 can be connected to the conductive contact 208. The working electrode 204 and the counter electrode 206 can each receive a voltage applied to respective conductive contacts 208, 210 by the battery 216 electrically connected to the circuit 214 and supply an electrical current to the conductive contacts 208, 210 based on reactions occurring in the person's interstitial fluid. The electrical current can be detected and a strength of the current may indicate an amount of glucose present in the person's interstitial fluid. The transmitter 212 can transmit glucose sensor data, activity data (e.g., data about the person's activity detected by the activity sensor 202), or other data to a remote device (e.g., the computing device 224). The remote device can receive the data and analyze the data (e.g., analyze the data to determine an effect of an activity on the amount of glucose present in the person's interstitial fluid or a correlation between the activity and the amount of glucose in the person's interstitial fluid). The remote device can also determine whether to output an alarm based on the effect of the activity on the amount of glucose in the person's interstitial fluid or the correlation between the activity and the amount of glucose in the person's interstitial fluid.

In some examples, the disposable biosensor 200 can be a continuous biosensor. For example, a voltage can be continuously applied to the working electrode 204 and the counter electrode 206 over a period of time (e.g., five hours) and the GOX on the distal portion of the working electrode 204 may continuously react with glucose in the person's interstitial fluid over the period of time. The disposable biosensor 200 can transmit glucose sensor readings periodically over the period of time for monitoring the amount of glucose in the person's interstitial fluid. The disposable biosensor 200 can also transmit activity data detected by the activity sensor 202 over the period of time for determining or monitoring an effect of one or more activities on the amount of glucose present in the person's interstitial fluid. In some examples, monitoring the effect of one or more activities on the amount of glucose present in the person's interstitial fluid or a correlation between the activities and the amount of glucose in the person's interstitial fluid can help the person manage a disease or illness. As an example, the person may be diabetic and monitoring the effect of one or more activities on the amount of glucose in the person's interstitial fluid can allow the person to monitor blood glucose levels before or after such activities, which may enhance an effectiveness of diabetes treatment efforts.

The computing device 224 can be communicatively coupled to the disposable biosensor 200 for receiving data and can include a processor 226, a memory 228, and a bus 230. The memory 228 can also include instructions 232 executable by the processor 226 for operating the computing device 224. The computing device 224 can also include a database 234, a display device 236, a communication device 238, and an antenna 240.

The processor 226 can be communicatively coupled to the memory 228 via the bus 230. The memory 228 can include any type of memory device that retains stored information when powered off. The computing device 224 uses the processor 226 and the memory 228 to execute software for obtaining information from the disposable biosensor 200 and store such information in the memory 228 or in a database 234. The display device 236 can provide a user interface and can provide sensor information that has been obtained from the disposable biosensor 200.

The communication device 238 can be a radio transmitter or transceiver. In some examples, the communication device 238 can be an RFID transceiver that emits RF signals to the disposable biosensor 200, which then transmits sensor data to the computing device 224. In some examples, other suitable computing devices 224 according to this disclosure may have other types of radio receivers or transceivers, such as an NFC transceiver, a BlueTooth™ transceiver, or a wireless local area network ("WLAN") transceiver, such as a WiFi transceiver. Selection of the appropriate communication device 238 for the computing device 224 may depend on a type of the transmitter 212 within the disposable biosensor 200.

In some examples, the computing device 224 receives sensor data such as, for example, glucose sensor data, activity data (e.g., data about the person's activity detected by the activity sensor 202), or other data from the disposable biosensor 200. The computing device 224 can determine one or more parameters associated with the person's activity based on the data received from the disposable biosensor 200. As an example, the activity sensor 202 can be an accelerometer that detects the person's motion during an activity and data about the person's motion is transmitted to the computing device 224, which executes processor executable instructions 232 stored in the memory 228 to determine a number of steps taken by the person during the activity based on the data.

In some examples, the computing device 224 receives sensor data from the disposable biosensor 200 and stores the sensor data in the memory 228 or in a database 234. The computing device 224 may store the sensor data along with a time stamp or time indicator associated with the data. As an example, the computing device 224 can receive glucose sensor data from the disposable biosensor 200 and a time stamp associated with the glucose sensor data, and store the glucose sensor data, along with the time stamp in the database 234. As another example, the computing device 224 can receive activity data from the disposable biosensor 200 and a time stamp associated with the activity data, and store the activity data, along with the time stamp in the database 234. In some examples, the computing device 224 may generate a time stamp associated with sensor data received by the computing device 224 when the computing device 224 receives the sensor data, but, in other examples, the computing device 224 may receive a time stamp associated with sensor data from the disposable biosensor 200.

In some examples, the computing device 224 may execute instructions 232 to determine an effect of a particular activity on the amount of glucose present in the person's interstitial fluid or a correlation between the activity and the amount of glucose in the person's interstitial fluid. As an example, the computing device 224 can receive data about the person's activity over a period of time (e.g., thirty minutes) and a time stamp or a series of time stamps associated with the data received (e.g., a time stamp indicating a length of the period of time or one or more time stamps corresponding to an interval of time within the time period). The computing device 224 can store the data and the associated time stamps in the database 234. The computing device can also receive glucose sensor data over the period of time, along with one or more time stamps associated with the glucose sensor data and store the glucose sensor data and the one or more time stamps in the database 234. The computing device 224 can execute instructions 232 for comparing the time stamps associated with the activity data to the time stamps associated with the glucose sensor data for determining a correlation between the activity and the amount of glucose in the person's interstitial fluid. For example, the computing device 224 can compare activity data associated with a particular time of day with glucose sensor data associated with the same time of day to determine the correlation between the activity and the amount of glucose in the person's interstitial fluid at that time of day.

In another example, the computing device 224 can receive sensor data from the disposable biosensor 200 that indicates the person's activity, along with glucose sensor data indicating the amount of glucose in the person's interstitial fluid during the activity. The computing device 224 can generate a time stamp associated with the sensor data and store the sensor data, along with the time stamp in the database 234. The computing device 224 can receive the sensor data over a period of time and execute instructions 232 for aggregating the sensor data. The computing device 224 can also execute instructions 232 for comparing data about the person's activity to data about the person's glucose sensor readings over the period of time to determine an effect of the activity on the amount of glucose present in the person's interstitial fluid.

In some examples, the computing device 224 can determine whether to output an alarm based on the correlation between the activity and the amount of glucose in the person's interstitial fluid or based on the effect of the activity on the amount of glucose present in the person's interstitial fluid. For example, the computing device 224 can output the alarm in response to determining that the activity caused the amount of glucose in the person's interstitial fluid to be below a threshold. As another example, the computing device 224 may not output an alarm in response to determining that the activity has a minimal effect on the amount of glucose in the person's interstitial fluid.

In some examples, the memory 222 of the disposable biosensor 200 can include instructions, which can be executed by the processing device 220 to perform one or more operations for determining an effect of a particular activity on the amount of glucose present in the person's interstitial fluid or a correlation between the activity and the amount of glucose in the person's interstitial fluid in substantially the same manner as described above with respect to the computing device 224. The memory 222 of the disposable biosensor 200 can also include instructions, which can be executed by the processing device 200 to perform one or more operations for determining whether to output an alarm based on the correlation between the activity and the amount of glucose in the person's interstitial fluid or based on the effect of the activity on the amount of glucose present in the person's interstitial fluid in substantially the same manner as described above with respect to the computing device 224.

Figure 3:
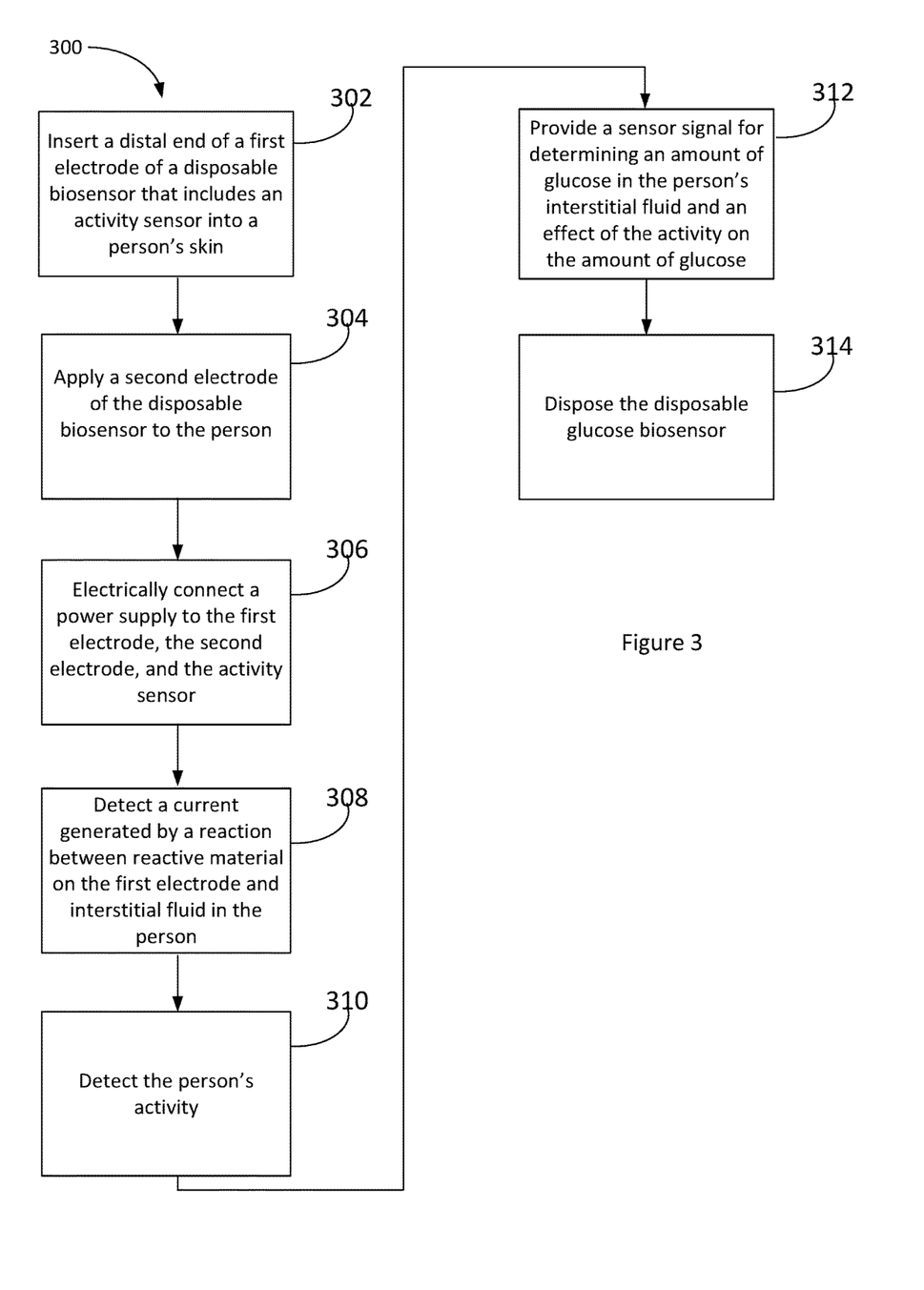
FIG. 3 shows an example of a method of using a disposable glucose biosensor that includes an activity sensor.

FIG. 3 shows an example of a method 300 of using a disposable glucose biosensor that includes an activity sensor. The method of FIG. 3 will be described with respect to the example disposable biosensor 200 shown in FIG. 2; however, the method is not limited to such a disposable biosensor 200. Rather, the method may be performed with any suitable disposable biosensor that includes an activity sensor according to this disclosure.

At block 302, a distal end of a first electrode 204 of a disposable biosensor 200 that includes an activity sensor 202 is inserted into a person's skin (e.g., into a subcutaneous layer beneath the person's skin). The distal end of the first electrode 204 can be inserted into the person's skin at a forty-five degree angle or any other suitable angle.

As discussed above with respect to FIGS. 1-2, in some examples, the first electrode 204 is a working electrode and the distal end of the first electrode 204 that is inserted into the person's skin includes a reactive material. The reactive material can be any reactive substance used to sense biological information, which may react when the distal end is inserted into the person's skin. For example, the reactive material can be a glucose oxidase ("GOX") coating and upon inserting the distal end into the person's skin and immersing the GOX in the person's interstitial fluid, the GOX on the first electrode 204 can react with the interstitial fluid, which can create a reaction product such as, for example, hydrogen peroxide. In this illustrative example, the reactive material is glucose oxidase, but in other examples, other suitable reactive materials may be applied on the distal end of the first electrode 204 based on the application or use of the disposable biosensor 200.

At block 304, a second electrode 206 of the disposable biosensor 200 can be applied to the person. In some examples, the second electrode 206 can be an Ag/AgCl material that can be applied to the person by coating or otherwise disposing the second electrode 206 on a portion of the first electrode 204 and inserting the first electrode 204, along with the second electrode 206, into the person's skin. Thus, in some examples, the insertion of the second electrode 206 may occur substantially simultaneously with the insertion of the working electrode 204.

In another example, the second electrode 206 is applied to the person by attaching a portion of the second electrode to a surface of the person's skin. For example, the second electrode 206 can be an Ag/AgCl patch that can be attached to the surface of the person's skin.

In still another example, the second electrode 206 can be applied to the person by inserting a portion of the second electrode 206 into the person's skin (e.g., in to the subcutaneous layer beneath the person's skin). For example, the second electrode 206 can include an Ag/AgCl wire or substrate (e.g., a metal or plastic substrate) coated with Ag/AgCl that can be inserted into the subcutaneous layer at a distance away from the first electrode 204.

At block 306, a power supply is electrically connected to the first electrode 204, the second electrode 206, and the activity sensor 202 of the disposable biosensor 200. For example, a circuit 214 can be electrically connected to a battery 216. The circuit 214, along with the battery 216, can be electrically connected to the first electrode 204, the second electrode 206, and the activity sensor 202 prior to applying the disposable biosensor 200 to the person. In another example, the circuit 214, along with the battery 216, may be electrically connected to the first electrode 204, the second electrode 206, and the activity sensor 202 after the first electrode 204 or the second electrode 206 is applied to the person. The battery 216 can provide a voltage to the circuit 214. The circuit 214 can be electrically connected to the conductive contacts 210, 208, which are connected to the first electrode 204 and second electrode 206, respectively, to apply the voltage to the first electrode 204 and the second electrode 206. The circuit 214 can also be connected to the activity sensor 202 to provide the voltage to the activity sensor 202.

In some examples, the method 300 does not include block 306. For example, the circuit 214, along with the battery 216, can be permanently connected to the first electrode 204, the second electrode 206, and the activity sensor 202 (e.g., during manufacture of the disposable biosensor 200) such that a user of the disposable biosensor 200 may not need to electrically connect a power supply to the first electrode 204, the second electrode 206, and the activity sensor 202.

At block 308, a current generated by a reaction between the reactive material and glucose in the interstitial fluid of the person is detected, e.g., by a microcontroller or other logic within the disposable biosensor 200. For example, based on the voltage applied to the first electrode 204 and the counter electrode 206 (e.g., by the battery 216), a current may be generated based on the reaction between glucose in the person's interstitial fluid and the reactive material (e.g., GOX) on the first electrode 204. The current can then be provided to the conductive contacts 208, 210, which can be detected by the disposable biosensor 200.

At block 310, data about the person's activity is detected by the activity sensor 202. In some examples, the activity sensor 202 becomes enabled or turned on in response to the person's activity and detects data about the activity. For example, the activity sensor 202 can be an accelerometer that detects the person's motion when the person begins to move, e.g., when they walk, jog, or run, and enables itself in response to motion.

The activity sensor can also detect and provide data about the activity and the data can be used to determine one or more parameters associated with the activity such as for, example, a type of the activity (e.g., whether the person is walking or running) an intensity of the activity (e.g., an acceleration of the person while the user is engaged in the activity), a number of steps taken by the person during the activity, a duration of the activity, a temperature of the person during the activity, a heart rate of the person, a respiration rate of the person during the activity, a resting respiration rate of the person after the activity, an amount of sweat produced by the person during the activity, etc.

As an example, the activity sensor 202 can be an accelerometer that detects the person's motion when the user is running and provides data about the person's motion to a remote device (e.g., a computing device 224) and the remote device can determine whether the person is running or walking based on the data about the person's motion. As another example, the activity sensor 202 can be a galvanic skin response sensor that can be used to measure electrical conductance of the person's skin during the activity, which may vary based on a moisture level of the person's skin (e.g., may vary based on an amount of sweat on the person's skin). In some examples, data about the electrical conductance of the person's skin during the activity may be provided to the remote device, which can determine an amount of sweat produced by the person during the activity based on the data. The amount of sweat produced by the person during the activity may be used to determine an intensity of the activity or a type of the activity. As an example, the remote device may determine that the person engaged in a high intensity activity based on the user producing a large amount of sweat during the activity. In some examples, multiple activity sensors may be employed, and each may provide one or more signals associated with detected activity.

At block 312, a sensor signal from the disposable biosensor 200 is provided to a transmitter 212, which can be a radio frequency ("RF") transmitter. In some examples, the disposable biosensor 200 can transmit the sensor signal to a remote device (e.g., the computing device 224) via the transmitter 212 and an antenna 218. In one example, the transmitter 212 may transmit sensor signals irrespective of a presence of a remote device (e.g., the computing device 224), but in some examples, the transmitter 212 may transmit sensor signals in response to the presence of an RFID or NFC signal from the remote device.

In some examples, the sensor signal can be transmitted to the remote device for determining the person's glucose levels. For example, the sensor signal can include data corresponding to a strength of the current detected by the disposable biosensor 200 (e.g., in block 308) or an amount of glucose detected within the person's interstitial fluid. In some examples, the strength of the current detected by the disposable biosensor 200 may indicate an amount of glucose present in the person's interstitial fluid.

The sensor signal can also be transmitted to the remote device for determining one or more parameters associated with a detected activity (e.g., an activity detected at block 310) or an effect of a detected activity on an amount of glucose present in the person's interstitial fluid. For example, the sensor signal can include data indicating the person's motion over a period of time (e.g., twenty-four hours) and the computing device 224 can aggregate or compile the data. The computing device 224 may execute one or more operations for determining a number of steps taken by the person over the period of time based on the person's motion over the period of time. The computing device 224 may also execute one or more operations for determining a correlation between the number of steps taken by the person over the period of time and the amount of glucose present in the person's interstitial fluid over the period of time. Based on the correlation, the computing device 224 may determine an effect of the detected activity (e.g., the number of steps taken by the user over the period of time) on the amount of glucose present in the person's interstitial fluid.

In some examples, the sensor signal can be transmitted to the remote device to monitor the effect of one or more detected activities on the amount of glucose present in the person's interstitial fluid or a correlation between the detected activities and the amount of glucose in the person's interstitial fluid, which can help the person manage a disease or illness. As an example, the person may be diabetic and monitoring the effect of one or more activities on the amount of glucose in the person's interstitial fluid can allow the person to monitor blood glucose levels before or after such activities, which may enhance an effectiveness of diabetes treatment efforts.

In some examples, the remote device can determine whether to output an alarm based on the correlation between the detected activities and the amount of glucose in the person's interstitial fluid or based on the effect of the detected activities on the amount of glucose present in the person's interstitial fluid. For example, the remote device can output the alarm in response to determining that the detected activities are causing the amount of glucose in the person's interstitial fluid to drop below a threshold. As another example, the remote device may not output an alarm in response to determining that the detected activities have a minimal effect on the amount of glucose in the person's interstitial fluid.

In some examples, the method 300 of using a disposable biosensor 200 that includes an activity sensor 202 includes, at block 314, disposing the disposable biosensor 200. In some examples, the disposable biosensor 200, along with the activity sensor 202, can be disposed after the disposable biosensor 200 is used for a period of time. As an example, the disposable biosensor 200 can be disposed after a period of five days or after any suitable period of use. As another example, the disposable biosensor 200, along with the activity sensor 202, can be disposed after a sensor signal is provided to a remote device.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Some example disposable biosensors including an activity sensor according to this disclosure may include a processor. The biosensors may include a computer-readable medium, such as a random access memory ("RAM") coupled to the processor. The processor can execute computer-executable program instructions stored in memory, such as executing one or more computer programs. Such processors may include a microprocessor, a digital signal processor ("DSP"), an application-specific integrated circuit ("ASIC"), field programmable gate arrays ("FPGAs"), and state machines. Such processors may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

Such processors may include, or may be in communication with, media, for example computer-readable storage media, that may store instructions that, when executed by the processor, can cause the processor to perform the steps described herein as carried out, or assisted, by a processor. Examples of computer-readable media may include, but are not limited to, a memory chip, ROM, RAM, ASIC, or any other medium from which a computer processor can read or write information. The processor, and the processing described, may be in one or more structures, and may be dispersed through one or more structures. The processor may include code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

That which is claimed is:

1. A disposable biosensor comprising:
   a glucose sensor comprising:
   a first electrode having a distal end insertable into a subcutaneous layer beneath a patient's skin, the first electrode having a reactive material disposed on the distal end;
   a second electrode comprising a counter electrode to the first electrode; and wherein the glucose sensor is configured to provide glucose sensor data;
   an activity sensor to sense activity and provide an activity sensor data, the activity sensor data comprising information about a physical movement of the patient;
   wherein, a sensor data comprises both glucose sensor data provided by said glucose sensor and activity sensor data provided by said activity sensor;
   a memory;
   a processor to:
   receive the sensor data;
   generate a time stamp for said sensor data; and
   store activity information based on the activity sensor data, and glucose information based on the glucose sensor data in the memory with the generated time stamp; and
   a radio frequency ("RF") transmitter in communication with the first and second electrodes and the activity sensor to transmit biosensor information, wherein the activity sensor, the first electrode, and the second electrode are included in the disposable biosensor.

2. The disposable biosensor of claim 1, wherein the reactive material comprises a glucose oxidase material.

3. The disposable biosensor of claim 1, wherein the activity sensor comprises at least one of an accelerometer, a gyroscope, a heart rate sensor, a galvanic skin response sensor, an inertial measurement unit, or a temperature sensor.

4. The disposable biosensor of claim 1, wherein the information about the physical movement of the patient comprises at least one of: a duration of the physical movement, a number of steps taken by the patient during the physical movement, a heart rate of the patient, a respiration rate of the patient, an intensity of the physical movement, or an amount of sweat produced by the patient during the physical movement.

5. The disposable biosensor of claim 1, further comprising:
a battery electrically coupled or couplable to the first and second electrodes, the activity sensor, and the RF transmitter to apply a voltage across the first and second electrodes and to the activity sensor and RF transmitter, the voltage for generating a current for determining an amount of glucose in interstitial fluid under the patient's skin.

6. The disposable biosensor of claim 5, further comprising:
a memory; and
a processor to receive the glucose sensor data from the first or second electrodes and the activity sensor data from the activity sensor and to transmit the sensor data to the RF transmitter.

7. The disposable biosensor of claim 1, wherein the RF transmitter is further to transmit the sensor data and the time stamp to a remote device.

8. The disposable biosensor of claim 1, wherein:
the first electrode comprises platinum; and
the second electrode comprises a silver/silver-chloride material.

9. A method comprising:
inserting a distal end of a first electrode of a disposable glucose biometric sensor into a subcutaneous layer beneath a patient's skin, the disposable glucose biometric sensor comprising an activity sensor and the first electrode having a reactive material disposed on the distal end;
applying a second electrode of the disposable glucose biometric sensor to the patient, the second electrode comprising a counter electrode to the first electrode;
wherein, a sensor data comprises both glucose biometric sensor data provided from said glucose biometric sensor and activity sensor data provided from an activity sensor;
wherein, a sensor data comprises both glucose biometric sensor data provided from said glucose biometric sensor and activity sensor data provided from an activity sensor,
the glucose biometric sensor data indicating the patient's glucose level, and;
the activity sensor data comprising information about a physical movement of the patient;
receiving said sensor data;
generating a time stamp for said sensor data; and
storing activity information based on the activity sensor data, and glucose information based on the glucose biometric sensor data in a memory with the generated time stamp,
wherein the activity sensor, the first electrode, and the second electrode are included in the disposable glucose biometric biosensor.

10. The method of claim 9, wherein the reactive material comprises a glucose oxidase material.

11. The method of claim 9, wherein the activity sensor signal further comprises at least one of: a duration of the physical movement of the patient, a number of steps taken by the patient during the physical movement, a heart rate of the patient, a respiration rate of the patient, or an amount of sweat produced by the patient during the physical movement.

12. The method of claim 9, further comprising transmitting the activity information, the glucose information, and the generated time stamp to a remote device.

13. The method of claim 12, wherein the transmitting is performed using a radio frequency identification ("RFID") or near-field communication ("NFC") technique.

14. The method of claim 9, wherein:
the first electrode comprises platinum; and
the second electrode comprises a silver/silver-chloride material.

15. The disposable biosensor of claim 1, wherein the activity sensor is enabled to provide the activity sensor signal to be transmitted in response to sensing activity.

16. The disposable biosensor of claim 1, further comprising a battery electrically connected to, and configured to supply electrical power to, the first and second electrodes and the activity sensor.

17. The disposable biosensor of claim 16, wherein the disposable biosensor is configured to provide the stored activity information, glucose information, and the generated time stamp after the battery is depleted.

* * * * *